Aug. 12, 1958 C. H. FISCHER Plant Pat. 1,741
GLADIOLUS PLANT
Filed Dec. 16, 1957
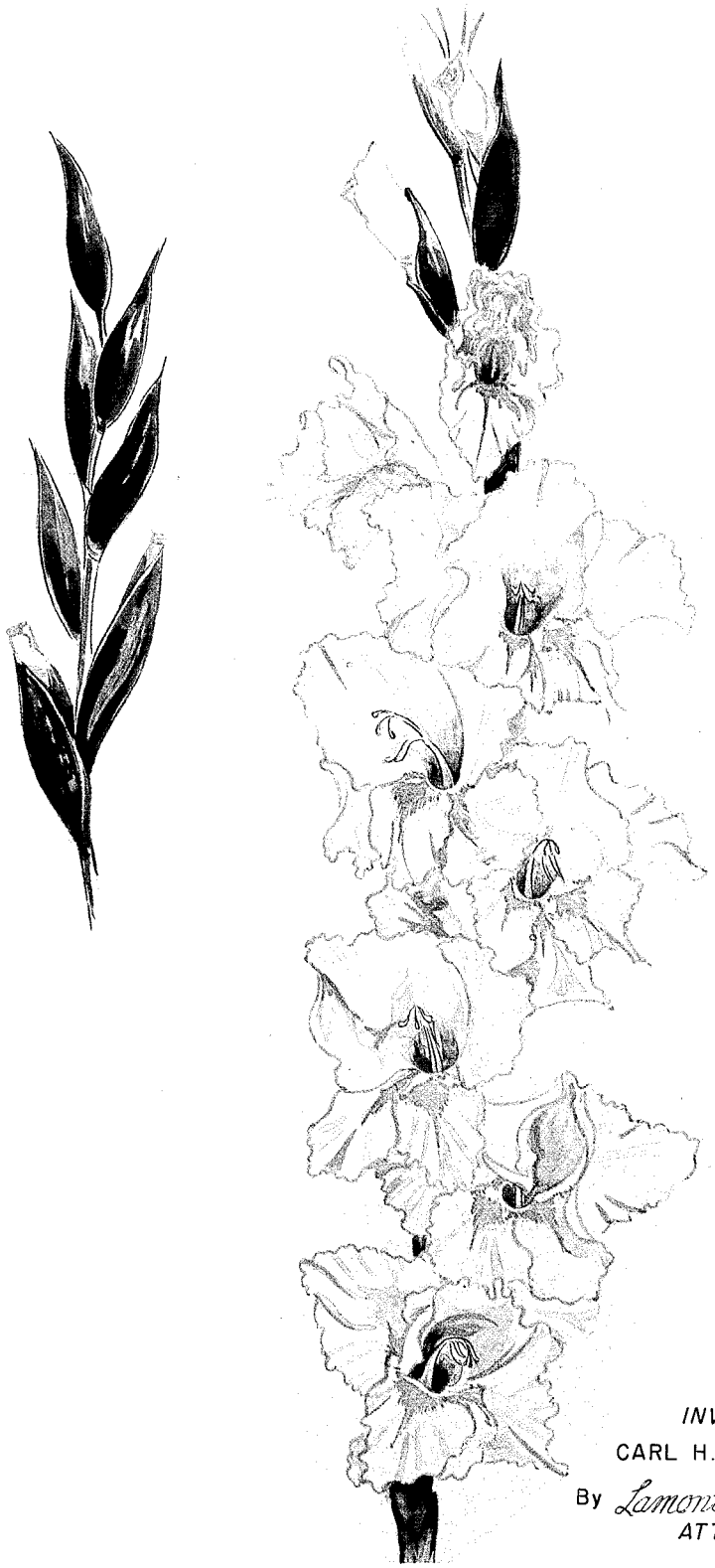
INVENTOR
CARL H. FISCHER
By Lamont Johnston
ATTORNEY United States Patent Office Plant Pat. 1,741

Patented Aug. 12, 1958

1,741

GLADIOLUS PLANT

Carl H. Fischer, St. Charles, Minn., assignor to Selected Glads, Inc., Nashville, Tenn., a corporation of Tennessee Application December 16, 1957, Serial No. 703,230

1 Claim. (Cl. 47—60)

My present invention relates to a new and improved variety of gladiolus and is notable particularly for its unusual needlepointed form and its novel combination of colors of red and yellow. I have identified this new variety as seedling No. 535–51 in my breeding work.

To the best of my knowledge, this new variety is the result of a cross between the varieties Crown Jewel, unpatented, and Pactolus, unpatented, Crown Jewel being the seed parent and Pactolus the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proved to be permanently fixed.

The illustration, made a part of this application, shows two views of a single bloom spike of this new variety, reduced in size, and is as nearly true to color as it is possible to depict. The view to the right shows the lower part of the spike and the view to the left shows the upper part. The illustration shows how many of the petals like to roll back, making the appearance that the petals come to a point, a feature described as needlepointing. The illustration also shows the shape and symmetry of the spike as well as the unusual red blotch on a yellow background.

In the following detailed description, color plate references are to the "Horticultural Colour Chart," by The British Colour Council. Where there are other references to color, the ordinary dictionary meanings of the terms are intended.

*The plant*

Growth: Very vigorous, averaging 48 inches in height and sometimes attaining a height of 52 inches. Propagates readily.

Blooming: Each spike opens from 5 to 7 four-inch flowers at one time. Successive blooms open, totalling an average of seventeen florets to each spike. The variety is an early bloomer, blooming on the average in 75–80 days from large bulbs.

Stems: Straight; stiff. Diameter at base is ½" to ¾".

Foliage: Deep green; average leaf is 1½ inches wide and the plant is 24 inches high.

Disease resistance: This variety is very resistant to disease. It has been found resistant to Sclerotina Dry Rot, Septoria Leaf Spot and Fusarium Yellows to which some other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases, whereas this variety remained healthy and unaffected.

Corms: Unusually healthy and high crowned. Average 2 inches in diameter from adult plants.

*The flower*

Spike: Long, slender, has 16 to 18 buds and opens 3 to 4 flowers the first day, following which 5 to 7 are open at one time until all have opened.

Bud:

*Size.*—Opening buds are 2 to 2½ inches long.

*Opening.*—8 to 9 show color at one time, 3 to 4 opening the first day.

Flower:

*Arrangement.*—Flowers are alternately spaced on the spike and all face in the same direction.

*Size.*—Lower blooms average 4 inches across when permitted to bloom on the plant in the field. Upper blooms are progressively smaller.

*Form.*—Wide open; recurved and ruffled. 6 petals; 3 upper ones larger than the 3 lower ones.

*Keeping qualities.*—Keeps and opens well.

Petals:

*Shape.*—Petals are elongated, ruffled, recurved, needlepointed and occasionally twisted.

*Size.*—Three upper petals are 1½ inches to 2 inches in diameter; lower petals 1 to 1½ inches wide.

*Aspect.*—Substance is heavy; surface is smooth and ruffled at edges.

*Fragrance.*—None.

*Color.*—The largest area of the flower is Primrose Yellow 601/2. The blotch is Geranium Lake 20 edged with Lemon Yellow 4/1. A dash of the blotch may extend onto other petals rather than on the lips only.

Reproductive organs:

*Stamens.*—Large, light yellow.

*Pistils.*—Three-pronged, extending about the same distance as the stamens. Cream.

*Comparisons*

My new variety resembles Ares, unpatented, more than any other known variety, but differs from it principally as follows:

(1) My variety is taller than Ares.

(2) My variety is of a deeper color than Ares.

(3) My variety has a larger, rounder, sharper, deeper blotch than Ares.

(4) My variety is ruffled and has a more distinctive form than Ares.

(5) My variety propagates better than Ares.

(6) My variety has a greater third dimension in floret form than Ares. The florets are more gracefully poised on the stem.

Having thus disclosed my invention, I claim:

The new and distinct variety of gladiolus plant substantially as herein shown and described, characterized by its vigorous growth, its novel combination of contrasting colors, the lacy, graceful arrangement of florets on the stem and the needlepointing of its petals.

No references cited.